(12) United States Patent
Li et al.

(10) Patent No.: US 8,084,737 B2
(45) Date of Patent: Dec. 27, 2011

(54) ARRAY-BASED ION STORAGE SYSTEM AND METHOD THEREFOR

(75) Inventors: Yuanjing Li, Beijing (CN); Zhiqiang Chen, Beijing (CN); Qingjun Zhang, Beijing (CN); Hua Peng, Beijing (CN); Zhude Dai, Beijing (CN); Shaoji Mao, Beijing (CN); Dexu Lin, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 411 days.

(21) Appl. No.: 12/318,343

(22) Filed: Dec. 24, 2008

(65) Prior Publication Data

US 2010/0065755 A1 Mar. 18, 2010

(30) Foreign Application Priority Data

Dec. 27, 2007 (CN) .......................... 2007 1 0304329

(51) Int. Cl.
*H01J 27/00* (2006.01)

(52) U.S. Cl. ..................... 250/292; 250/423 R; 250/424

(58) Field of Classification Search .................. 250/281, 250/286–288, 291, 292, 282, 423 R, 424
See application file for complete search history.

(56) References Cited

U.S. PATENT DOCUMENTS

| | | | |
|---|---|---|---|
| 5,200,614 A | | 4/1993 | Jenkins |
| 6,124,592 A | | 9/2000 | Spangler |
| 6,906,324 B1 | * | 6/2005 | Wang et al. ..................... 250/292 |
| 6,933,498 B1 | * | 8/2005 | Whitten et al. ................. 250/287 |
| 7,154,088 B1 | * | 12/2006 | Blain et al. ..................... 250/292 |
| 7,449,686 B2 | * | 11/2008 | Wang et al. ..................... 250/292 |
| 2007/0029473 A1 | * | 2/2007 | Verentchikov ................. 250/281 |
| 2008/0017794 A1 | * | 1/2008 | Verbeck ......................... 250/292 |
| 2008/0128605 A1 | * | 6/2008 | Wells et al. ..................... 250/281 |

FOREIGN PATENT DOCUMENTS

CN 1544931 A 11/2004

* cited by examiner

*Primary Examiner* — Bernard E Souw
(74) *Attorney, Agent, or Firm* — Jacobson Holman PLLC

(57) ABSTRACT

An array-based ion storage system includes an ion generation section, and an ion storage section having a first end electrode coupled to the ion generation section and having multiple holes, a second end electrode having multiple holes, an intermediate electrode having multiple holes, a first insulator formed as a ring between the first end electrode and the intermediate electrode, and a second insulator formed as a ring between the intermediate electrode and the second end electrode. The ion storage section can be made thinner to facilitate consistency in ion extraction and reduce the spread of an ion mobility spectrum peak. The insulators have a big hole, and the ions cannot bump onto the insulation material during ion vibration or thermal movement in the storage space. Therefore, charge transfer and accumulation at the insulator and the subsequent discharge will not occur, suppressing instability of storage and loss of ions.

10 Claims, 2 Drawing Sheets

ARRAY-BASED ION STORAGE SYSTEM AND METHOD THEREFOR

BACKGROUND OF THE INVENTION

1. Field of Invention

The present invention relates to the field of safety inspection technology, in particular to an ion storage system and method for inspection equipment for inspecting drugs and explosives by means of ion mobility technique.

2. Description of Prior Art

An ion mobility spectrometer discriminates between different ions according to the fact that different ions have different velocities in a uniform weak electric field. The application of ion storage improves the sensitivity of the ion mobility spectrometer up to about an order of a pictogram. For the conventional ion storage as described in U.S. Pat. No. 5,200,614 and CN Patent 200310106393.6, for example, loss of ions occurs due to the poor boundary condition of the electrical field.

An ion storage trap used in a mass spectrograph is generally formed by end electrodes at both sides and a perforated intermediate electrode. The storage and extraction of ions are enabled by adjusting the voltages applied to the two end electrodes and the perforated intermediate electrode. Similarly to the ion storage trap used in the mass spectrograph, U.S. Pat. No. 6,124,592 provides a single ion storage method. In this method, however, the storage region has to be larger to meet the requirement of storage potential in the case of an ionization zone and a drift region each having a longer diameter. So, the ions have to travel a longer distance to exit from the storage region. This necessitates a longer gate-opening period and a higher volume. Further, inconsistency in the start points of different ions entering the drift region is increased.

U.S. Pat. No. 6,933,498 discloses an ion trap array-based storage solution to improve efficiency of ion storage. In this solution, between each of end electrodes and an intermediate electrode is sandwiched an insulator having holes, each of which corresponds to one ion storage trap. The ions may bump onto the insulator, causing charge transfer and accumulation and subsequent discharge. This will lead to instability in ion storage and degrade the sensitivity.

SUMMARY OF THE INVENTION

An object of the present invention is to provide an array-based ion storage system and method for an ion mobility spectrometer, which can greatly improve sensitivity and resolution.

In one aspect of the present invention, an array-based ion storage system is provided comprising: ion generation section; and ion storage section comprising a first end electrode coupled to the ion generation section and formed as having a plurality of holes, a second end electrode formed as having a plurality of holes, an intermediate electrode formed as having a plurality of holes, a first insulator formed in the shape of a ring and sandwiched between the first end electrode and the intermediate electrode to insulate them from each other, and a second insulator formed in the shape of a ring and sandwiched between the intermediate electrode and the second end electrode to insulate them from each other.

Preferably, each hole of the intermediate electrode has a diameter $D1$ as larger as one to two times of the thickness $L2$ of the storage section.

Preferably, $D1=\sqrt{2}\,L2$.

Preferably, the ion generation section comprises at least one of $^{63}$Ni, corona discharge source, laser, ultraviolet and X-ray.

Preferably, the ion generation section and the first end electrode are applied with a first voltage, the intermediate electrode is applied with a second voltage, and the second end electrode is applied with a fixed voltage.

Preferably, the array-based ion storage system further comprises a plurality of ring electrodes spaced apart from the second end electrode, the plurality of ring electrodes being applied with voltages changing uniformly.

Preferably, the first and second voltages can be floating, and a voltage difference exists between them.

In another aspect of the present invention, a method for a array-based ion storage system is provided, the array-based ion storage system is provided comprising: an ion generation section; and an ion storage section comprising a first end electrode coupled to the ion generation section and formed as having a plurality of holes, a second end electrode formed as having a plurality of holes, an intermediate electrode formed as having a plurality of holes, a first insulator formed in the shape of a ring and sandwiched between the first end electrode and the intermediate electrode to insulate them from each other, and a second insulator formed in the shape of a ring and sandwiched between the intermediate electrode and the second end electrode to insulate them from each other; the method comprises a storage step of applying a first voltage to the ion generation section and the first end electrode, applying a second voltage to the intermediate electrode, the second voltage being a RF voltage with DC bias component, and applying a fixed voltage to the second end electrode, wherein a voltage difference exists between the first voltage and the DC bias component of the second voltages so that a storage space for storing ions is formed at the intermediate electrode; and an extraction step of changing the first and second voltages to educe the ions stored in the storage space.

With the above solutions of the present invention, the ion storage section can be made thinner for an ordinary ion mobility spectrometer at the premise of meeting the voltage requirement for ion storage and causing no decrease in storage efficiency. The thinner ion storage section facilitates consistency in ion extraction, reduces the spread of ion mobility spectrum peak and refines the resolution.

In addition, the first and second insulators are formed as having a big hole, and thus the ions cannot bump onto the insulation material at both sides at the time of ion vibration or thermal movement in the storage space. Therefore, charge transfer and accumulation at the insulator and the subsequent discharge will not occur, suppressing instability of storage and loss of ions.

During the ion storage phase, positive or negative ions to be collected are driven by the electrical field and drift to the intermediate electrode of the array-based storage section, and forms here a number of non-electrical field zones, namely ion storage space. During the ion extraction phase, the voltages at the ion generation section and one of the end electrodes and the intermediate electrode of the array-based storage section are changed to drive the ions from the storage region to the drift region. After that, the overall voltages are immediately restored to those at the storage phase.

DETAILED DESCRIPTION OF PREFERRED EMBODIMENTS

Now, the present invention will be further described with reference to the figures and embodiments. The present invention can be applied in either a negative ion mode or a positive ion mode. For the purpose of conciseness and illustration, only the positive ion mode is specifically described here.

Figure 1:
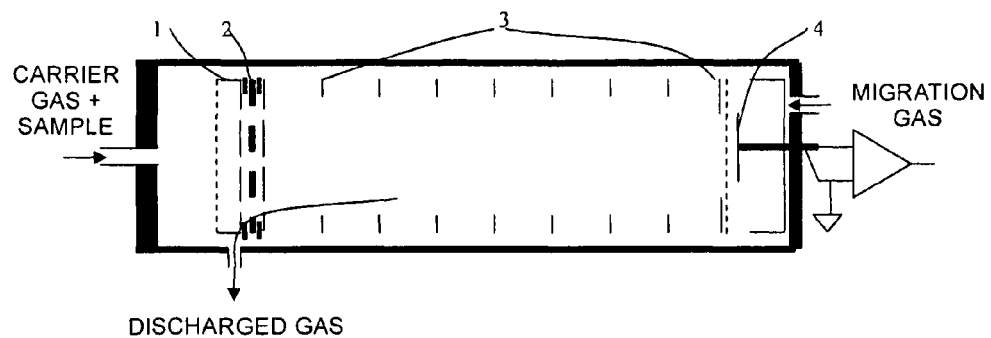
FIG. 1 is a schematic sectional diagram of an array-based ion storage system according to an embodiment of the present invention.
Figure 2:
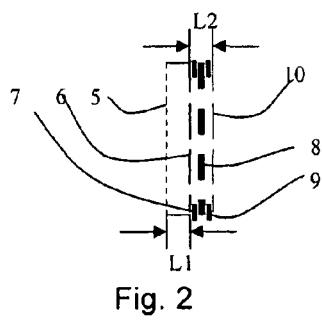
FIG. 2 is a schematic sectional diagram of an ionization zone and an array-based storage region in the system of FIG. 1.

As shown in FIGS. 1 and 2, the array-based ion storage system according to the present embodiment comprises an ion generation section 1, an array-based storage section 2, a group of ring electrodes 3 and a Faraday plate 4, etc.

The ion generation section 1 is an ionization source, such as nickel 63, corona discharge source, laser, ultraviolet and X-ray, etc.

Figure 3A:
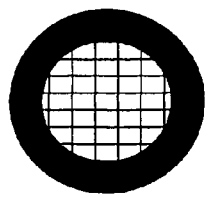
FIGS. 3A-3F are detailed configuration diagrams of the ionization zone and the array-based storage region shown in FIG. 2.
Figure 3B:
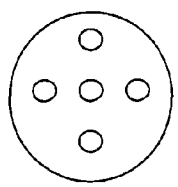
Figure 3C:
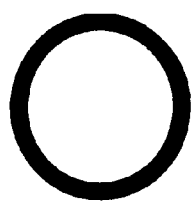
Figure 3D:
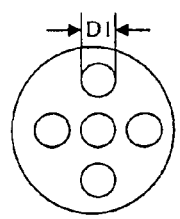
Figure 3E:
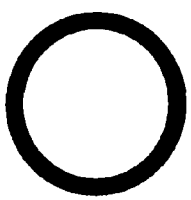
Figure 3F:
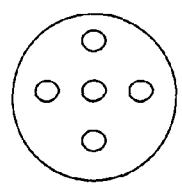

Referring to FIG. 2, the ion generation section 1 and the array-based storage section 2 are integrated together and comprise a mesh electrode 5 having a shape shown in FIG. 3A, a first end electrode 6 having a shape shown in FIG. 3B and multiple holes, a first ring insulator 7 having a shape shown in FIG. 3C, an intermediate electrode 8 having a shape shown in FIG. 3D and multiple holes, a second ring insulator 9 having a shape shown in FIG. 3E, and a second end electrode 10 having a shape shown in FIG. 3F and multiple holes, with these electrodes and insulator being arranged in this order.

As shown in FIGS. 2 and 3, the multiple holes on the two end electrodes 6, 10 and the intermediate electrode 8 are provided in one-to-one correspondence. The first and second insulators 7, 9 separate the first and second end electrodes 6, 10 from the intermediate electrode 8 only at their periphery portions and electrically insulate them from each other, respectively. There is only a single big hole at the center of each of the first and second insulators 7, 9, so that the two insulators 7, 9 are each formed as a ring insulator. Thanks to the insulation material with a big hole at both sides, ions cannot bump onto the insulation material at both sides at the time of ion vibration or thermal movement in the storage space. Therefore, charge transfer and accumulation at the insulator and the subsequent discharge will not occur, suppressing instability of storage and loss of ions.

Further, the ion generation section 1 is coupled mechanically and electrically to one side of the array-based storage section 2, which is constructed as being thin to facilitate consistency in ion extraction and reduce the spread of ion mobility spectrum peak. The voltages applied to the ion generation section 1 and the first end electrode 6 and the intermediate electrode 8 of the array-based storage section 2 differ from each other by certain voltage differences and can be floating. The second end electrode 10 of the array-based storage section 2 is applied with a fixed voltage, and the ring electrodes 3 are applied with voltages changing uniformly to produce a drift region.

The holes on the above end electrodes are preferably shaped as a circle. Also, holes of any other shape can be used, such as hexagon, square, etc. For each hole, D1 is preferably one to two times of L2, L2 is less than 5 mm, and $D1=\sqrt{2}L2$ is preferred. Here, D1 represents the diameter of each circular hole on the intermediate electrode 8 or the effective diameter of each hole having any other shape. L2 represents a gap between the two end electrodes 6 and 10. D1 and L2 can be selected according to practical applications.

Figure 4:
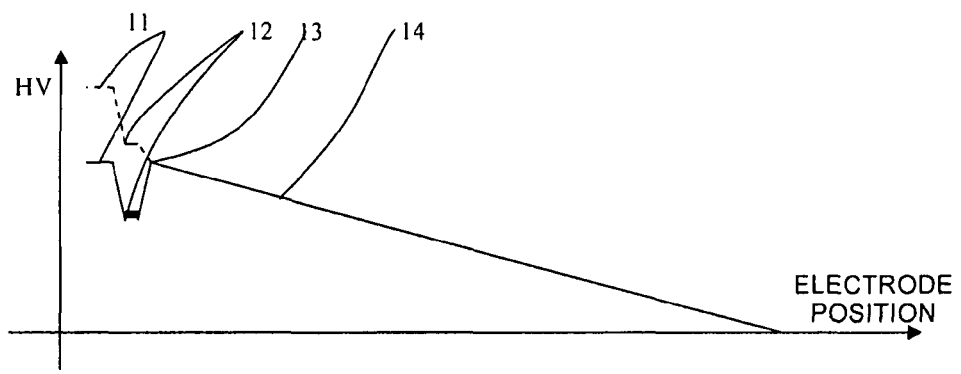
FIG. 4 is a schematic diagram showing the potentials of respective electrodes when the system according to an embodiment of the present invention operates in a positive ion mode.

Referring to FIGS. 2 and 4, reference symbol 11 denotes the voltage applied to the ion generation section 1 and the first end electrode 6, reference symbol 12 denotes the DC bias component of the RF voltage applied to the intermediate electrode 8, and the voltages 11, 12 can be floating. In addition, the second end electrode 10 is applied with a fixed voltage 13. The ring electrodes 3 are applied with voltages 14 decreasing uniformly to produce the drift region. The dashed line in FIG. 4 denotes the voltages at respective points during the ion extraction phase, the solid line denotes the voltages at respective points during the ion storage phase, and the solid line 14 denotes the voltages at respective points in the drift region, which voltages remain unchanged at the storage and extraction phases.

At the ion storage phase, the voltage 11 is applied to both of the first and second end electrodes 6 and 10, and the RF voltage 12 having a DC bias voltage lower than the voltage 11 is applied to the intermediate electrode 8. As a result, the positive ions will move to the position where the potential well 12 is formed and be stored there. Further, the frequencies and amplitudes of the bias voltage and RF voltage components in the voltage 12 can be adjusted to produce a potential well of a suitable depth. In other words, during the ion storage phase, the positive or negative ions to be collected are driven by the electrical field and drift to the intermediate electrode 8 of the array-based storage section 2, and forms here a number of non-electrical field zones, namely ion storage space.

When the voltages 11, 12 applied to the first end electrode 6 and the intermediate electrode 8 are raised from the level of the solid line to the level of the dashed line, and the RF voltage component in the voltage 12 is turned off, the ions are driven and guided into the drift region for drifting and discrimination. Subsequently, the overall voltages are restored to those at the storage phase.

Figure 5:
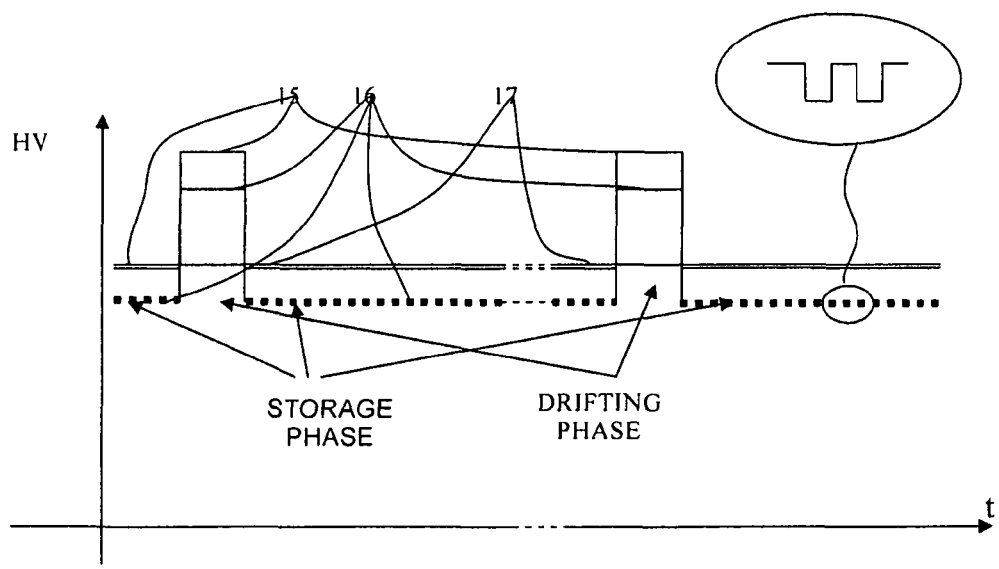
FIG. 5 is a schematic diagram showing voltage variation vs. time of the respective electrodes when the system according to an embodiment of the present invention operates in a positive ion mode.

In FIG. 5, reference symbol 15 denotes that the wave form of the voltage applied to the ion generation section 1 and the first end electrode 6 varies over time, reference symbol 16 denotes that the wave form of the voltage applied to the intermediate electrode 8 varies over time, and reference symbol 17 denotes that the wave form of the voltage applied to the second end electrode 10 varies over time.

At the storage phase, the voltages 15 applied to the ion generation section 1 and the first end electrode 6 are identical and higher than the voltage 16 applied to the intermediate electrode 8. The expanded view of the upper right corner of FIG. 5 shows the RF voltage wave form superposed with the DC bias voltage. The wave form can be square wave, sine wave, sawtooth wave and the like. The ions are stored in a plurality of non- or zero-electrical field zones at the intermediate electrode 8.

At the ion extraction phase, the voltages 15 applied to the ion generation section 1 and the first end electrode 6 and the voltage 16 applied to the intermediate electrode 8 are each higher than the voltage 17 applied to the second end electrode 10. Meanwhile, the AC component is removed from the voltage 16. The ions are driven out of the storage regions and enter the drift region.

With the above solutions of the present invention, the ion storage section can be made thinner for an ordinary ion mobility spectrometer at the premise of meeting the voltage requirement for ion storage and causing no decrease in storage efficiency. The thinner ion storage section facilitates consistency in ion extraction, reduces the spread of ion mobility spectrum peak and refines the resolution.

In addition, the insulation material of the first and second insulators 7, 9 has big holes convenient to ion movement, and thus the ions cannot bump onto the insulation material at both sides at the time of ion vibration or thermal movement in the storage space. Therefore, charge transfer and accumulation at the insulator and the subsequent discharge will not occur, suppressing instability of storage and loss of ions.

During the ion storage phase, positive or negative ions to be collected are driven by the electrical field and drift to the intermediate electrode 8 of the array-based storage section 2, and forms here a number of non-electrical field zones, namely ion storage space. During the ion extraction phase, the voltages at the ion generation section 1 and the first end electrode 6 and the intermediate electrode 8 of the array-based storage section 2 are changed to drive the ions from the storage regions to the drift region. After that, the overall voltages are immediately restored to those at the storage phase.

The foregoing description is only the preferred embodiments of the present invention and not intended to limit the present invention. Those ordinarily skilled in the art will appreciate that any modification or substitution in the principle of the present invention shall fall into the scope of the present invention defined by the appended claims.

What is claimed is:

1. An array-based ion storage system comprising:
   an ion generation section; and
   an ion storage section including
      a first end electrode coupled electrically to the ion generation section and formed as having a plurality of holes,
      a second end electrode formed as having a plurality of holes,
      an intermediate electrode formed as having a plurality of holes,
      a first insulator formed in a shape of a ring and sandwiched between the first end electrode and the intermediate electrode to insulate the first end electrode and the intermediate electrode from each other, and
      a second insulator formed in the shape of a ring and sandwiched between the intermediate electrode and the second end electrode to insulate the second end electrode and the intermediate electrode from each other.

2. The array-based ion storage system of claim 1, wherein each of the holes of the intermediate electrode has a diameter D1 equal to from one to two times a gap L2 between the two end electrodes.

3. The array-based ion storage system of claim 2, wherein D1=√2 L2.

4. The array-based ion storage system of claim 1, wherein the ion generation section includes at least one of nickel 63, a corona discharge source, a laser, an ultraviolet source, and an X-ray source.

5. The array-based ion storage system of claim 1, wherein the ion generation section and the first end electrode are applied with a first voltage, the intermediate electrode is applied with a second voltage, and the second end electrode is applied with a fixed voltage.

6. The array-based ion storage system of claim 5, further comprising a plurality of ring electrodes spaced apart from the second end electrode, the plurality of ring electrodes being applied with voltages changing uniformly.

7. The array-based ion storage system of claim 5, wherein the first and second voltages are floating, and a voltage difference exists therebetween.

8. A method for an array-based ion storage system
   having an ion generation section, and an ion storage section that includes
      a first end electrode coupled electrically to the ion generation section and formed as having a plurality of holes,
      a second end electrode formed as having a plurality of holes,
      an intermediate electrode formed as having a plurality of holes,
      a first insulator formed in a shape of a ring and sandwiched between the first end electrode and the intermediate electrode to insulate the first end electrode and the intermediate electrode from each other, and
      a second insulator formed in the shape of a ring and sandwiched between the intermediate electrode and the second end electrode to insulate the second end electrode and the intermediate electrode from each other;
   the method comprising:
      a storage step of applying a first voltage to the ion generation section and the first end electrode, applying a second voltage to the intermediate electrode, the second voltage being an RF voltage with a DC bias component, and applying a fixed voltage to the second end electrode, a voltage difference existing between the first voltage and the DC bias component of the second voltages so that a storage space for ions is formed at the intermediate electrode; and
      an extraction step of changing the first and second voltages to educe the ions stored in the storage space.

9. An array-based ion storage system comprising:
   an ion generation section; and
   an ion storage section including
      a first end electrode coupled electrically to the ion generation section, and having a plurality of holes therein,
      a second end electrode having a plurality of holes therein,
      an intermediate electrode having a plurality of holes therein,
      a first insulator configured as a ring having one central aperture, the first insulator being located between the first end electrode and the intermediate electrode to insulate the first end electrode and the intermediate electrode from each other, and
      a second insulator configured as a ring having one central aperture, the second insulator being located between the intermediate electrode and the second end electrode to insulate the second end electrode and the intermediate electrode from each other.

10. The array-based ion storage system according to claim 9, wherein the central aperture has a diameter that is substantially equal to each of a diameter of a pattern of the plurality of holes in the first end electrode, a diameter of a pattern of the plurality of holes in the intermediate electrode, and a diameter of a pattern of the plurality of holes in the second end electrode.

* * * * *